US00PP22510P2

(12) United States Plant Patent
Dirr

(10) Patent No.: US PP22,510 P2
(45) Date of Patent: Feb. 21, 2012

(54) ***GARDENIA AUGUSTA* PLANT NAMED 'PIIGA-I'**

(50) Latin Name: ***Gardenia augusta* L.**
Varietal Denomination: PIIGA-I

(75) Inventor: Michael Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 0 days.

(21) Appl. No.: 12/925,880

(22) Filed: Nov. 1, 2010

(51) Int. Cl.
*A01H 5/00* (2006.01)

(52) U.S. Cl. ..... Plt./255

(58) Field of Classification Search ..... Plt./255
See application file for complete search history.

(56) References Cited

U.S. PATENT DOCUMENTS

PP19,988 P3 5/2009 Dirr

OTHER PUBLICATIONS

Page 12 of Plant Introductions, Inc. booklet showing *Gardenia Augusta* 'PIIGA-I' as distributed to wholesale growers from Jan. 2010.

*Primary Examiner* — Annette Para
(74) *Attorney, Agent, or Firm* — Greenlee Sullivan P.C.

(57) ABSTRACT

A new and distinct cultivar of *Gardenia augusta* plant named 'PIIGA-I', characterized by its large, single white flowers that are produced from spring to frost, lustrous, dark green foliage, compact rounded growth habit, and cold hardiness to USDA Hardiness Zone 6b.

3 Drawing Sheets

Genus and species of plant claimed: *Gardenia augusta* L.
Variety denomination: 'PIIGA-I'

BACKGROUND OF THE INVENTION

The present invention relates to a new and distinct cultivar of *Gardenia augusta*, a member of the Rubiaceae family, hereinafter referred to by its cultivar name 'PIIGA-I'. This cultivar is grown primarily as an ornamental for landscape use and for use as a potted plant.

The cultivar originated from open-pollination of *Gardenia augusta* 'MADGA I' (U.S. Plant Pat. No. 19,988) in Dearing, Ga., and was selected from the progeny by continued evaluation for floral characteristics, growth habit, and cold hardiness.

'PIIGA-I' has been asexually reproduced by softwood cuttings in Watkinsville, Ga. since 2005, and the characteristics of the cultivar have been stable and reproduced true-to-type in successive vegetative generations.

SUMMARY OF THE INVENTION

'PIIGA-I' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIGA-I' from all other varieties in commerce known to the inventor. 1) Large, single white flowers that are produced from spring to frost. 2) Lustrous, dark green foliage. 3) Compact rounded growth habit. 4) Cold hardiness to USDA Hardiness Zone 6b.

'PIIGA-I' is distinguished from its female parent 'MADGA I' by its vigor, growth habit, flower size, foliage size, fruit production, and cold hardiness. 'PIIGA-I' has a more vigorous and larger growth habit than 'MADGA I'. 'PIIGA-I' has larger flowers and foliage than 'MADGA I'. 'PIIGA-I' produces less fruit than 'MADGA I'. 'PIIGA-I' is more cold hardy than 'MADGA I' based on field testing in Watkinsville, Ga. and Louisville, Ky. There are no other cultivars of *Gardenia augusta* with this combination of characteristics known to the inventor.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Gardenia.*

DETAILED DESCRIPTION

Figure 1:
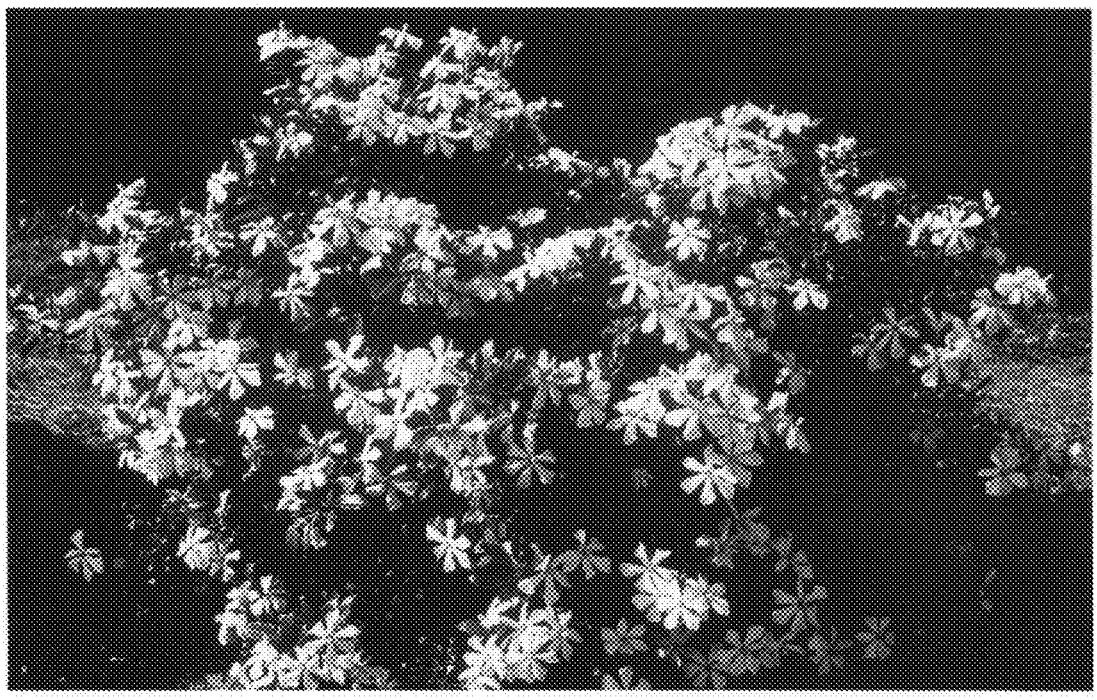
FIG. 1 shows the overall appearance of a mature plant of 'PIIGA-I'.
Figure 2:
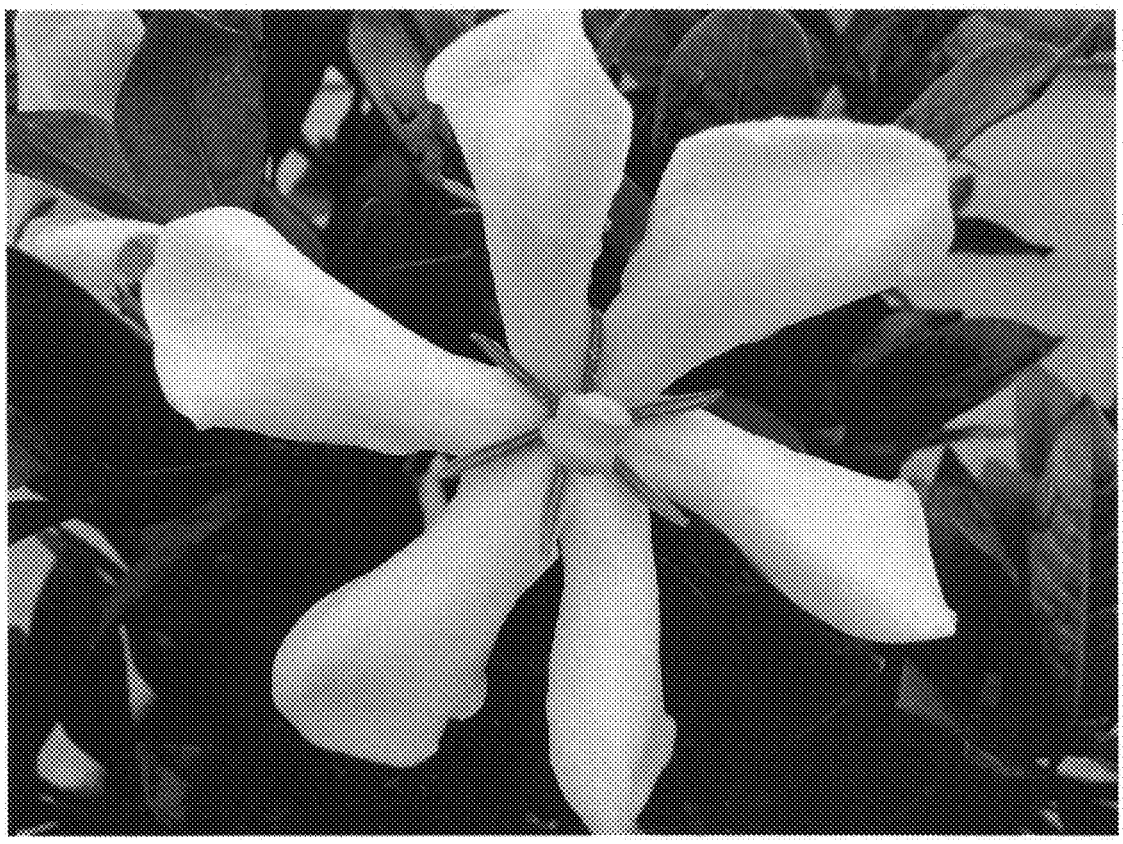
FIG. 2 shows a close-up view of a flower of 'PIIGA-I'.
Figure 3:
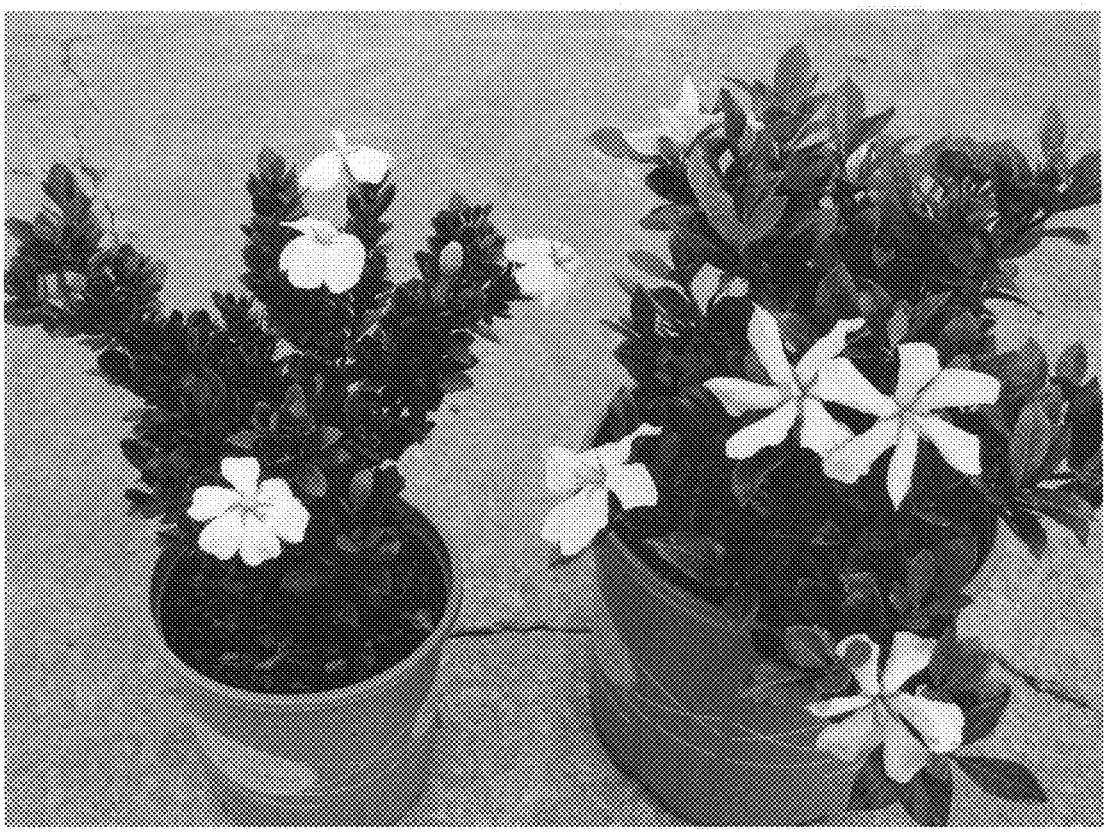
FIG. 3 shows a comparison of the growth habit, foliage size, and flower size of 'PIIGA-I' (right) to 'MADGA I' (left).

In the following description, color references are made to The Royal Horticultural Society Colour Chart, 2001 Edition, except where general terms of ordinary dictionary significance are used. Plants used for the description were approximately 2 years old and were grown in 11.8 L containers in full sun under outdoor conditions in Watkinsville, Ga.

Botanical classification: 'PIIGA-I' is a cultivar of *Gardenia augusta*. Parentage: The current variety is a progeny from an open-pollination of *Gardenia augusta* 'MADGA I' (U.S. Plant Pat. No. 19,988).

Plant description:

The claimed variety is a freely branching, rounded, evergreen shrub. The plant is hardy in USDA Zones 6b to 9.

*Propagation*.—Stem cuttings. Time to initiate roots in summer: about 4 weeks.

*Root description*.—Numerous, fibrous, and well-branched.

*Plant size*.—The original plant, planted in the ground, was about 75 cm high from the soil level to the top of the foliage and about 75 cm wide after about 5 years.

*First year stems having a diameter of about* 3 *mm*.—Shape: round. Pubescence: finely hairy.

*First year stem color* (*young*).—143A. Color (woody): 199B.

*Stem strength*.—Flexible when young, easily broken once mature.

*Internode length*.—About 2.2 cm.

*Second year and older stems have a diameter of about* 5 *mm or more*.—Shape: round. Pubescence: none.

*Second year and older stem color*.—199B.

*Bark*.—Some stringy exfoliation beginning on second year stems.

*Trunk diameter*.—about 1.5 cm at the soil line. Color: N200A.

Vegetative bud description:

*Vegetative buds*.—Arrangement: opposite. Shape: conical, single-scaled. Size: about 3 mm in length, about 1 mm in width; Color: 143A.

Foliage description:

*Arrangement*.—Opposite. Length: about 5.5 cm. Width: about 2.7 cm.

*Shape*.—Elliptical. Apex: acuminate. Base: cuneate. Margin: entire to revolute.

*Texture* (*upper and lower surfaces*).—Glabrous, lustrous, no pubescence.

*Venation*.—Pinnate. Venation color (upper and lower surfaces): 144B.

*Color of emerging leaves*.—144A on the upper surface, and 144B on the lower surface. Color of mature leaves: 139A on the upper surface, and 146B on the lower surface.

*Petiole length*.—About 2 mm. Petiole diameter: about 2 mm. Petiole texture: glabrous. Petiole color (upper and lower surfaces): 144B.

Flower description:

*Flower type and habit*.—Flowers are borne singly at the terminals. Individual flowers are showy for about 3 days and remain on the plant for about 1 to 2 weeks after they have senesced. Bloom period: spring to frost. Flowers are produced prolifically from May to June, and then sporadically until October in Watkinsville, Ga. Fragrance: Exceedingly sweet fragrance.

*Flower diameter*.—about 7.5 cm.

*Flower bud diameter*.—About 1 cm. Flower bud length: about 2.5 cm. Flower bud shape: oblong. Flower bud color: 144A.

*Pedicels*.—About 2 cm in length, glabrous, and 144A.

Petals:

*Quantity*.—6, occasionally 7, petals per flower.

*Petal length*.—about 3.7 cm. Petal width: about 1.5 cm at the base to about 2.5 cm at the widest point.

*Petal shape*.—Obovate to spatulate with entire margin. Petal texture: thick, glabrous.

*Petal color*.—At peak bloom the upper and lower surfaces are 155C.

Stamens:

*Quantity*.—6 per flower. There is no separate filament structure present. Anthers: about 1 cm long and about 2 mm wide. Color: 199A. Pollen: produced in small quantities and color is 8B.

Pistils:

*Quantity/arrangement*.—One per flower, superior. Pistil length: about 4.5 cm. Pistil diameter: about 5 mm. Stigma shape: obovate, about 5 mm in diameter. Stigma color: 154C. Style: color is 154D, about 2.5 cm in length, and tubular in shape. Ovary: color is 160D, about 2 cm in length, oval in shape, and contains many (100 or more) very small (less than 1 mm) ovules.

Fruit:

*Type/appearance*.—Six-winged berry, oval in shape. Fruit length: about 2.5 cm. Fruit diameter: about 2 cm. Fruit color at maturity: 165B. Quantity: fruit is produced sporadically and the number of fruit per plant varies depending on the size and maturity of the plant. Seeds: rounded in shape, about 2.5 mm in diameter, 164C in color, and each berry contains many seeds, about 100 or more.

Disease/pest resistance:

No specific pest or disease resistance or susceptibility has been observed.

I claim:

1. A new and distinct *Gardenia augusta* plant named 'PIIGA-I', substantially as illustrated and described herein.

* * * * *